US00PP14912P3

(12) United States Plant Patent

Pecota et al.

(10) Patent No.: US PP14,912 P3
(45) Date of Patent: Jun. 15, 2004

(54) ORNAMENTAL SWEETPOTATO PLANT NAMED 'SWEET CAROLINE PURPLE'

(50) Latin Name: *Ipomoea batatas*
Varietal Denomination: Sweet Caroline Purple

(75) Inventors: Kenneth Pecota, Raleigh, NC (US); G. Craig Yencho, Washington, NC (US); Cynthia Pierce, Clayton, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/114,502

(22) Filed: Apr. 2, 2002

(65) Prior Publication Data

US 2003/0188361 P1 Oct. 2, 2003

(51) Int. Cl.[7] ..... A01H 5/00
(52) U.S. Cl. ..... Plt./258
(58) Field of Search ..... Plt./258

(56) References Cited

PUBLICATIONS

"Bodger Seeds/Botanicals," *Greenhouse Grower* (Jun. 2001).
Armitage, Allan M. and James M. Garner, "*Ipomoea batatas* 'Margarita,'" *HortScience*: 36(1) 178 (Feb. 2001).
Armitage, Allan M., "Sweet Potato," *Greenhouse Grower*: 103–104 (Mar. 1999).
Baggett, "Sweet potato vines are morning glory cousins," *Fine Gardening*: 84 (Apr. 2002).
Bodger Seeds, Ltd., "2001 Pack Trials" invitation, Apr. 3–12, 2001.
Bodger Seeds, Ltd., "2001 Pack Trials" brochure, p. 13, Apr. 3–12, 2001.
Bodger Botanicals catalog, Sep./Oct.: p. 6 (2001).
North Carolina State University, "New Sweet Potatoes Add Ornamental Flavor," *Extension's Successful Garden*: p. 1 (Mar. 2002).
Online catalog selling Ipomea cultivars: www.glasshouse-works.com/trop–ij.html p. 4 date of access: Aug. 15, 2002.
Online catalog selling Ipomea cultivars: www.sunnyfield-.com/varietylists/companionplants.html p. 5, date of access: Aug. 15, 2002.
Online catalog selling Ipomea cultivars: www.papgenos-.com/plantdh/plants.asp?catid=15 pp. 1–4, date of access: Aug. 15, 2002.
"Ornamental Sweet Potatoes," www.Inla.org/ornpotato.html pp. 1–2, updated Jun. 4, 2000, date of access: Aug. 15, 2002.

*Primary Examiner*—Kent Bell
(74) *Attorney, Agent, or Firm*—Myers Bigel Sibley & Sajovec, P.A.

(57) ABSTRACT

A new and distinct ornamental cultivar of *Ipomoea batatas* called 'Sweet Caroline Purple' is described that is a moderately compact, densely-mounding, plant with purple leaves that are deeply-lobed. The plant is distinguished by its short shoots and highly branched plant habit. Furthermore, this plant has excellent vigor and will flower under short day conditions. *Ipomoea batatas* 'Sweet Caroline Purple' is suitable for use in landscaping and containerized gardens.

5 Drawing Sheets

Latin name of the genus and species: The Latin name of the novel, ornamental plant variety disclosed herein is *Ipomoea batatas* (L.) Lam.

Variety denomination: The inventive cultivar of *Ipomoea batatas* disclosed herein has been given the variety denomination 'Sweet Caroline Purple'.

BACKGROUND OF THE INVENTION

*Ipomoea batatas* species are members of the morning glory family Convolvulaceae. *Ipomoea batatas*, commonly referred to as the white or yellow sweetpotato and the orange yam, are typically fast growing vines with palmately-lobed leaves. These ornamental species produce storage roots identical in appearance to the common sweet potato, but not as palatable. Late in the growing season, tubular flowers appear which are similar to morning glories, but plantings are dominated by the appearance of the foliage. The plants are highly desirable due to their ability to grow under varied stress conditions, cover a large space, and last the entire growing season. Moreover, these plants have few insect or disease problems.

Existing varieties of *Ipomoea batatas* are popular for landscaping applications. There are currently six common types of ornamental sweetpotatoes that are being cultivated primarily for annual, summer vines. These six cultivars are: 'Blackie' (unpatented), having dark purple-black foliage, lavender flowers, and edible storage roots; 'Terrace Lime' (unpatented) and 'Margarita' (unpatented; also known as 'Sulfur'), which have large brilliant chartreuse leaves and lavender blooms; 'Black Heart' (unpatented, also known as 'Ace of Spades'), having heart-shaped leaves with burgundy purple color; 'Tricolor' (unpatented, also known as 'Pink Frost'), is a variegated plant which has pale green, white, and pink-margined leaves; and 'Lady Fingers' (unpatented), which has medium green, dainty leaves divided into long, thin, fingerlike lobes which are complemented by burgundy stems and veins.

*Ipomoea batatas* 'Margarita' has recently been released in the United States, and has become widely used as a landscape annual. It is not suitable for mixed containers, as this variety exhibits a very vigorous growth and tends to outcompete other species. Another popular variety is 'Blackie', a vigorous purple-leaved clone which is also unsuited to containerized gardens. See Armitage. A. M. and J. M. Garner. 2001. *Ipomoea batatas* 'Margarita'. *HortScience* 36:178.

Therefore, to meet the current horticultural demand, it is desirable to produce new, more robust cultivars of ornamental sweetpotato with attractive foliage colors, leaf shapes, and plant architectures. In addition, it would be advantageous to develop cultivars of ornamental sweetpotato exhibiting a more compact growth, and which do not out-compete other species in mixed containers.

The present invention comprises a new and distinct variety of *Ipomoea batatas*, which has been named 'Sweet Caroline Purple'. The variety is suitable for use as a landscape or containerized plant.

Lineage. The *Ipomoea batatas* 'Sweet Caroline Purple' cultivar originated from a conventional cross between *Ipomoea batatas* cultivars Sulfur (the female parent; not patented) and Blackie (the male parent; not patented) conducted in the Winter of 1997–1998 at the Horticultural Greenhouses located at North Carolina State University, Raleigh, N.C. Seeds from this cross were planted in the Horticultural Greenhouses in Spring 1998 and in a field at North Carolina State University in June 1998. The single, individual plant now known as *Ipomoea batatas* 'Sweet Caroline Purple' was selected in October, 1998 because of its combination of exceptional features, and has been propagated asexually since that time.

Asexual Reproduction. Since its selection, *Ipomoea batatas* 'Sweet Caroline Purple' has been asexually reproduced at the Horticultural Greenhouses located at North Carolina State University, Raleigh, N.C. by vegetative propagation of vine cuttings. Asexual propagation of the new cultivar by cuttings at the location previously stated has shown that the unique features of this new Ornamental Sweetpotato are stable and the plant reproduces true to type in successive generations of asexual propagation.

SUMMARY OF THE INVENTION

The present *Ipomoea batatas* 'Sweet Caroline Purple' ornamental plant is a compact, densely-mounding cultivar producing many, short shoots. This cultivar is distinguishable from other cultivars by its purple leaves that have 3–5 deep lobes and a compact, highly branched plant habit. Furthermore, 'Sweet Caroline Purple' has a good vigor and will flower under short day conditions.

DETAILED BOTANICAL DESCRIPTION

The following is a detailed description of the botanical characteristics of a new and distinct cultivar of *Ipomoea batatas* plant known by the cultivar name *Ipomoea batatas* 'Sweet Caroline Purple'. All colors cited herein refer to The Royal Horticultural Society Colour Chart (The Royal Horticultural Society, London, 1995 edition) designations except where general terms of ordinary dictionary significance are used. Where dimensions, sizes, colors, and other characteristics are given, it is to be understood that such characteristics are approximations or averages set forth as accurately as practicable.

The descriptions reported herein are from ten-month-old plants grown individually in ten-inch azalea pots. The plants were grown in Raleigh, N.C., under commercial practice in a glass-covered greenhouse where, during the winter, day and night temperatures range between 18–30° C. and 15–21° C., respectively. Plant histories were taken in March 2002. *Ipomoea batatas* 'Sweet Caroline Purple' has not been observed under all possible environmental conditions; therefore, the phenotype may vary with variations in the environment such as season, temperature, light intensity, day length, cultural conditions, and the like.

Growth Conditions. *Ipomoea batatas* 'Sweet Caroline Purple' has excellent vigor, has a moderately fast growth rate, and is very adaptable to container culture. In locales with mild winter conditions, *Ipomoea batatas* 'Sweet Caroline Purple' will grow perennially; otherwise it is an annual plant that is killed by frost. In the greenhouse setting described above, after ten months of growth, plants of this cultivar produce compact, round-mounded, herbaceous plants averaging 18 cm in height and 108 cm in length. In containers grown outdoors, plants of this cultivar can be expected to grow to this size in eight to ten weeks. The growth habit of this plant is to grow upright with shoots growing outward. Similar to cultivated sweetpotatoes, wind or rain rarely causes much damage to 'Sweet Caroline Purple', but if damage does occur, the plant drops the damaged leaves and grows new shoots at nodes where the leaves were lost. Under low light levels in a greenhouse, 'Sweet Caroline Purple' can develop intumescence, which will remain on the affected foliage, but will be outgrown with new foliage.

Figure 1:
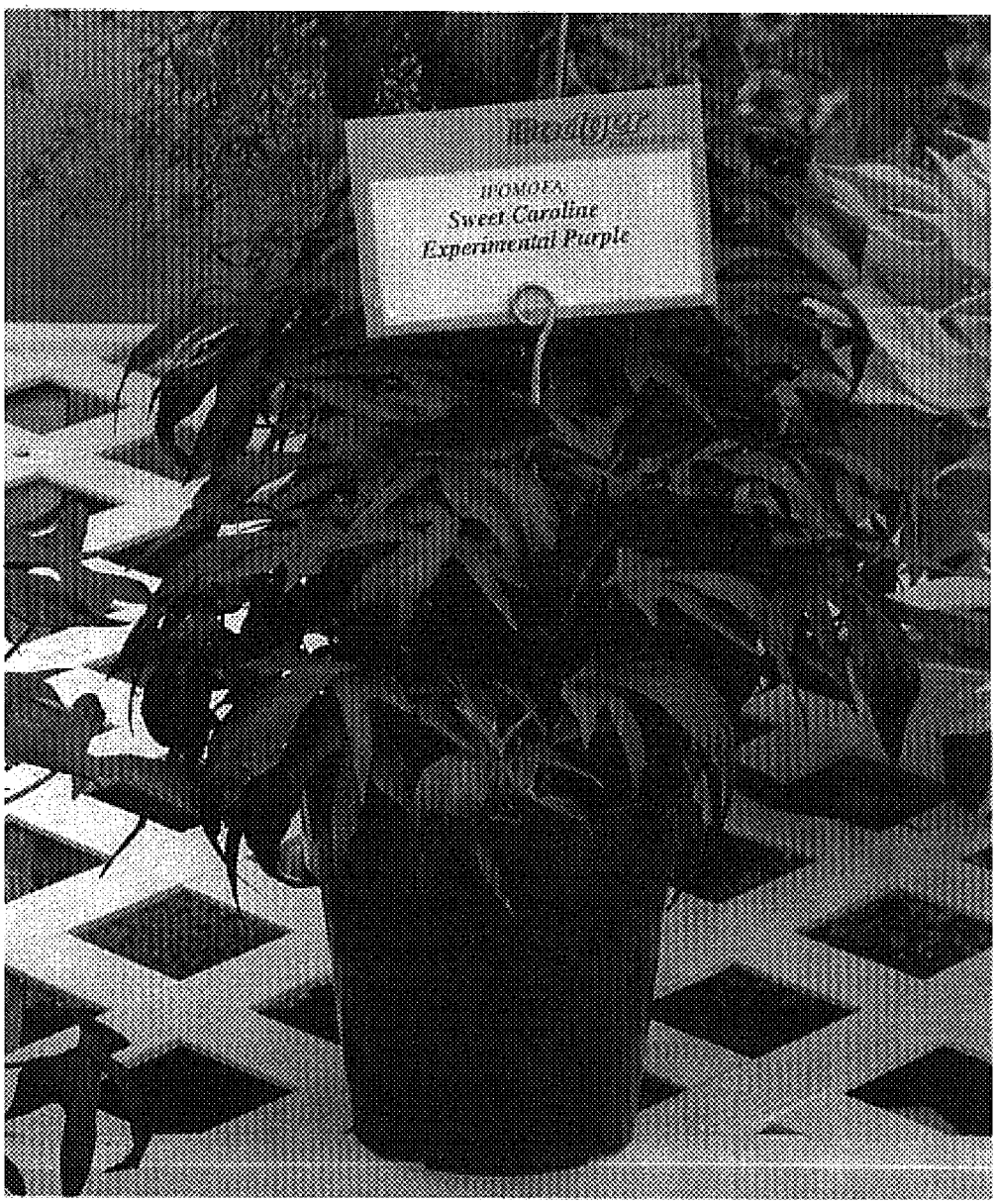
FIG. 1 is a color photograph of a typical plant of *Ipomoea batatas* 'Sweet Caroline Purple' grown in a container under commercial greenhouse conditions.
Figure 2:
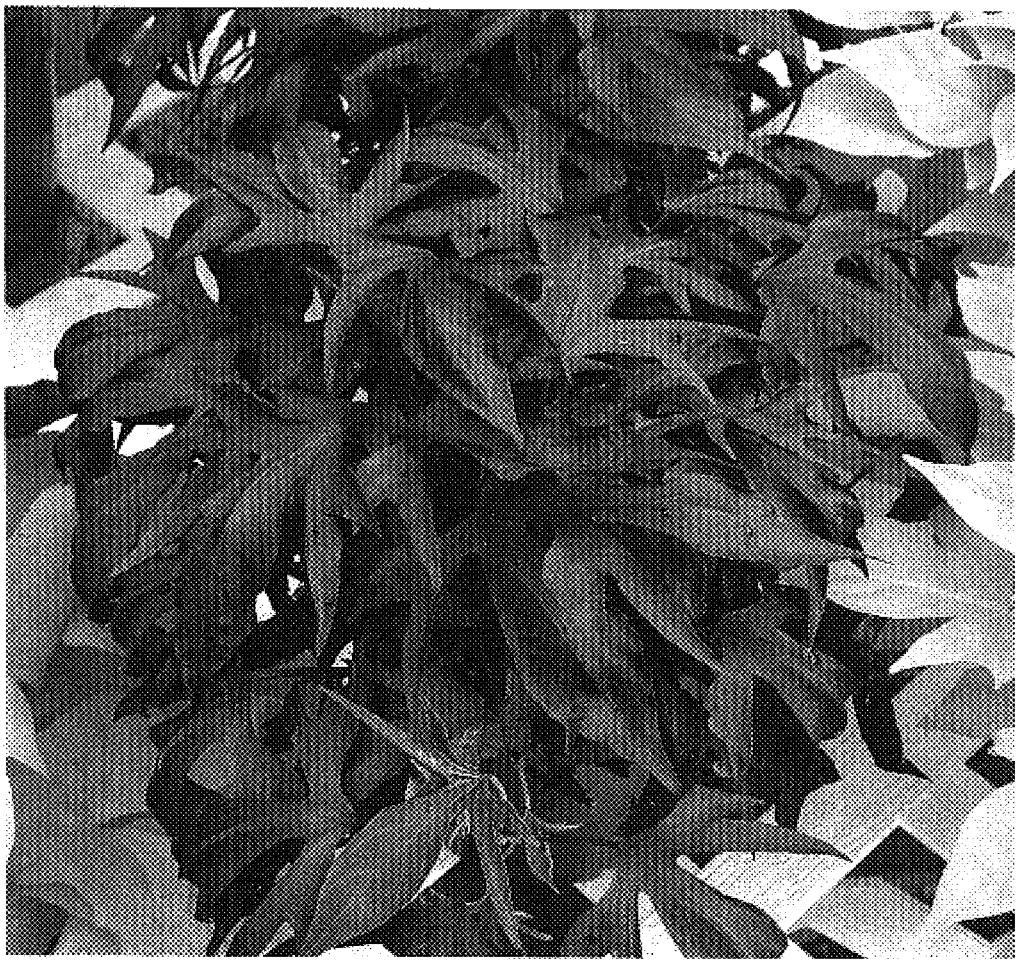
FIG. 2 shows a top view of a typical plant of the *Ipomoea batatas* 'Sweet Caroline Purple' grown in a container under commercial greenhouse conditions.

Above-Ground Structure and Coloration. FIGS. 1 and 2 show the shape and coloration of a typical plant of *Ipomoea batatas* 'Sweet Caroline Purple'. Color will vary somewhat due to temperature and nutrient stress, which affect the anthocyanin pigments (which give rise to the purple color). Overall, this cultivar is a compact, round-mounded, herbaceous plant that has an average height of 18 cm and an average area of spread of 108 cm. The growth habit of this plant is to grow upright with shoots growing outward.

Branching Habitat. Freely-branching with ~14 lateral branches coming off the stem. Very dense foliage with no pinching required to stimulate branching.

Stem (Color: 187A). Round and smooth with an outward and upward bending aspect and very good strength. Length: ~35 cm, Diameter: ~0.3 cm. Internodes are short with an average length of ~1.5 cm.

Vegetative Lateral Branches (Color: 187A). Same as stems for most characteristics. Length: ~35 cm. Diameter: ~0.3 cm. Internodes are short with an average length of ~1.5 cm. Many lateral branches are formed and each axil has latent shoots.

Petiole (Color: 187A). Length: ~8.4 cm. Diameter: ~0.2 cm.

Figure 3:
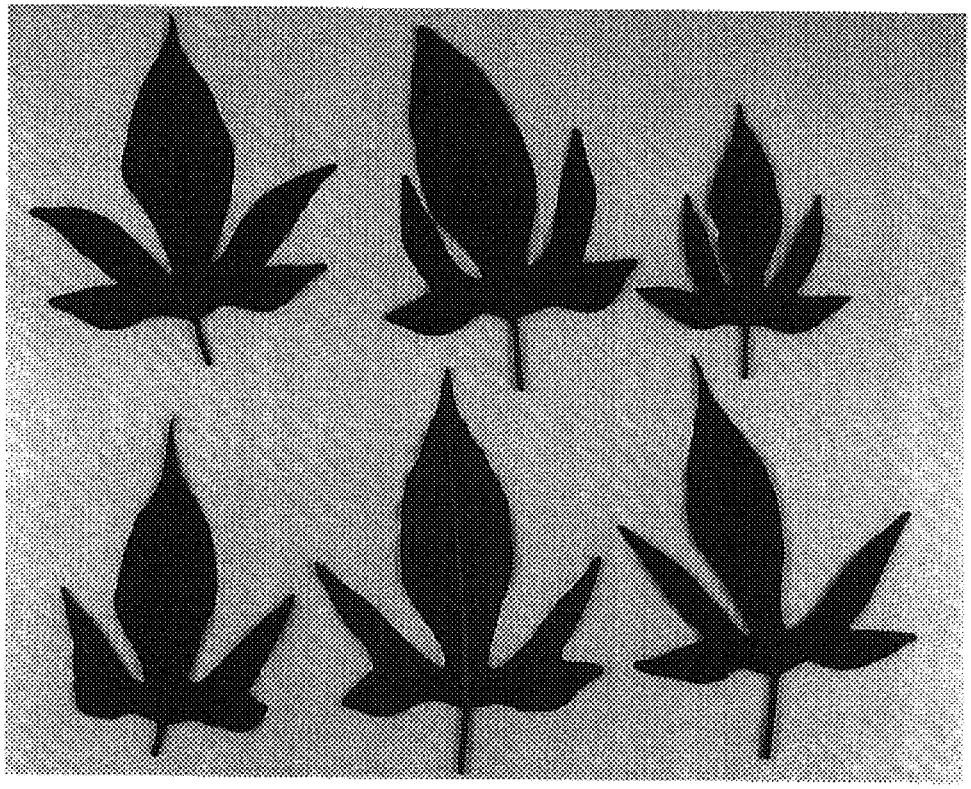
FIG. 3 shows the variety of leaves produced by *Ipomoea batatas* 'Sweet Caroline Purple' and the lower surface of the leaf (bottom row, center leaf).

Foliage. Leaves are alternate and simple. Further, the leaves are palmate and deeply divided into 3–5 lobes. Leaf shape is somewhat variable as is size (see FIG. 3). Quantity: Densely foliated, with ~16–18 leaves per lateral branch. Mature leaf length: ~9.3 cm. Mature leaf width: ~9.2 cm. Leaf margin is entire. Lobe width: ~1.4 cm. Mid-vein lobe length: ~7.9 cm. Mid-vein lobe width: ~2.9 cm. Leaf apex: Acute. Leaf base: Acute. Leaf has a smooth texture and matte finish. Venation is palmate at the base with arcuate veins in the center lamina. Color: Table 1. Leaves go from green to purple as they mature.

TABLE 1

| Leaf Structure | Upper Surface | Lower Surface |
|---|---|---|
| Young Leaf | 144A | 144A |
| Mature Leaf | 187A | 187A |
| Vein-mature leaf | 187A | 79A |
| Vein-young leaf | 144A | 144B |

Flowers. Flowers occur sporadically throughout the season in response to a variety of stressful conditions (e.g., drought, nutrient stress, cloudy weather). Flowering is enhanced by shorter day lengths, but the precise photoperiod for flower induction is currently unknown. The inflorescence is generally a cyme in which the peduncle is divided into two axillary peduncles. Each peduncle is further divided into two after the flower is produced. Peduncles are purple (Color: 187A), averaging around 90 mm long from mature leaf axils with an average diameter of 2.2 mm. Usually buds of the first, second and third order are developed, but sometimes single flowers are produced. Buds are cream colored (Color: 162D), ovate, and around 22 mm in length and 4.5 mm in diameter 24 hours before opening. The corolla is composed of five fused petals that form a funnel with a semi-stellate to pentagonal limb. Corolla width: ~4.0 cm, corolla length: ~3.9 cm. The corolla is not fragrant. The limb and outer throat are lavender and the inner throat purple. Inner limb color: 69C, Outer limb color: 69D, Inner throat color: 82A, Outer throat color: 69C. There are five sepals, with an average length of 10 mm and width of 4 mm. The sepals are ovate to elliptic in shape with an acute apex. Outer sepal color: 187A, Inner sepal color: 187B. Each flower has one pistil, with a cream colored style (Color: 155A) with a length averaging 15 mm. The stigma is cream colored (Color: 156D) and averages about 1.2 mm wide and 2 mm long and has two segments. The stigma is sometimes exerted and sometimes inserted relative to the stamens. The ovary is yellow (Color: 160B) and superior with two locules that contain one or two ovules. At the base of the ovary there are basal glands (Color: 167A) containing nectar. There are five cream colored anthers (Color: 158B) that are around 3 mm long. Pollen (Color: 158A) is scarce. No true seed have been produced although several hundred pollinations have been attempted, indicating very low, if any, fertility. There is some variation in flower size and color, depending on the environmental conditions. Descriptions are based on: CIP, AVRDC, IBPGR. 1991. Descriptors for Sweet Potato. Huaman, Z., editor. International Board for Plant Genetic Resources, Rome, Italy.

Figure 5:
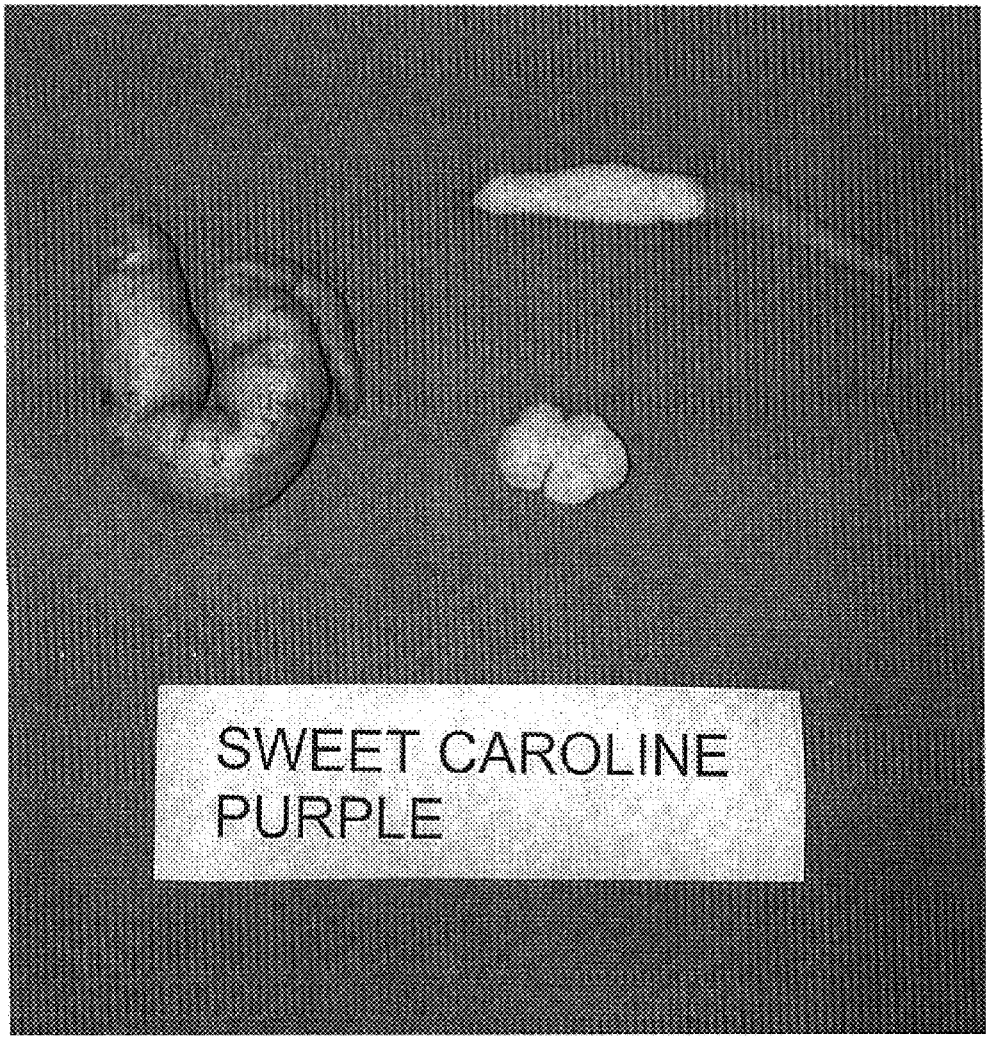
FIG. 5 shows the flesh and skin of storage roots.

Storage Roots. As shown in FIG. 5, the storage roots have a cream colored skin (Color: 158A) with cream-colored flesh (Color: 158A). Shapes are highly irregular and vary considerably in length and diameter depending on growing conditions. A minimum of 130 days are needed to produce storage roots that meet the size criteria for United States Department of Agriculture (USDA) US No. 1 grade (5.1–8.9 cm in diameter and 7.6 to 22.9 cm in length), but very few of these storage roots would meet the shape criteria for US No. 1 grade. Under conditions in which the plant grows perennially, the storage roots will continue to grow as long as the roots are healthy and the weather remains warm.

Figure 4:
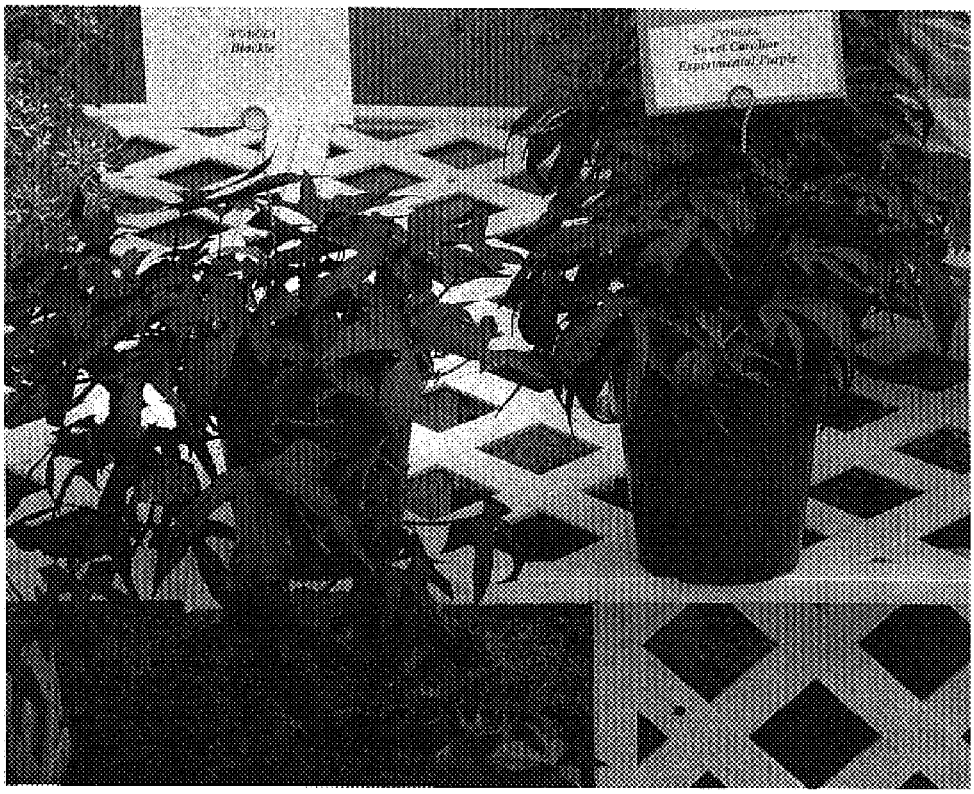
FIG. 4 provides a comparison of *Ipomoea batatas* 'Sweet Caroline Purple' (right) with the commercially available 'Blackie' cultivar (left). Note: 'Sweet Caroline Purple' was given the designation 'Sweet Caroline Experimental Purple' as shown in the figure during the testing period.

Comparison with Other *Ipomoea batatas* Cultivars. Of the six most common cultivars of ornamental sweetpotato, *Ipomoea batatas* 'Sweet Caroline Purple' most resembles 'Blackie'. Like 'Blackie', *Ipomoea batatas* 'Sweet Caroline Purple' has purple, deeply lobed leaves. However, 'Sweet Caroline Purple' has a moderately-compact plant habit compared with the trailing habit of 'Blackie' (FIG. 4). Furthermore, 'Sweet Caroline Purple' is highly branched compared with 'Blackie' resulting in a much denser foliage appearance. As compared with 'Blackie', 'Sweet Caroline Purple' has a more bunched and fuller appearance, which is more suitable for containerized propagation.

In a comparison with the parental strains, 'Sweet Caroline Purple' shares some attributes with its paternal parent (Table 2), but is also quite distinct therefrom and comprises a unique combination of characteristics.

TABLE 2

| | 'Sweet Caroline | Female Parent | Male Parent |
|---|---|---|---|
| Characteristic | Purple' | 'Sulfur' | 'Blackie' |
| Plant Habit | Moderately Compact | Trailing | Trailing |
| Foliage Color | Purple | Light Green | Purple |
| Leaf Size | Moderate | Large | Moderate |
| Leaf Shape | Deeply Lobed | Slightly Lobed | Deeply Lobed |
| Storage Root Skin Color | Cream (158A) | Purple (between 78A and 78B) | Cream (158B) |
| Storage Root Flesh Color | Cream (158A) | Cream (158A) | Cream (158A) |

Disease or Pest Resistance. 'Sweet Caroline Purple' is susceptible to Sweetpotato Feathery Mottle Virus and damage by Japanese beetles.

Herbarium vouchers. A voucher of 'Sweet Caroline Purple' will be deposited into the Herbarium of North Carolina State University (NCSU) in Raleigh, N.C. upon patenting.

What is claimed is:

1. A new and distinct cultivar of *Ipomoea batatas* plant named 'Sweet Caroline Purple', substantially as illustrated and described herein.

* * * * *